US010398343B2

(12) United States Patent
Murphy et al.

(10) Patent No.: US 10,398,343 B2
(45) Date of Patent: Sep. 3, 2019

(54) PERSPIRATION SENSOR

(71) Applicant: MC10, Inc., Lexington, MA (US)

(72) Inventors: Brian Murphy, Medford, MA (US); Valerie Susan Hanson, Medford, MA (US); Hoi-Cheong Steve Sun, Lexington, MA (US); Ping-Hung Wei, Burlingame, CA (US); Cole Papakyrikos, Brookline, MA (US); Alexander J. Aranyosi, Medford, MA (US); Ji Hyung Hong, Somerville, MA (US)

(73) Assignee: MC10, Inc., Lexington, MA (US)

( * ) Notice: Subject to any disclaimer, the term of this patent is extended or adjusted under 35 U.S.C. 154(b) by 604 days.

(21) Appl. No.: 15/057,762

(22) Filed: Mar. 1, 2016

(65) Prior Publication Data

US 2016/0256070 A1  Sep. 8, 2016

Related U.S. Application Data

(60) Provisional application No. 62/127,124, filed on Mar. 2, 2015.

(51) Int. Cl.
*A61B 5/00* (2006.01)
*A61B 5/053* (2006.01)
*A61B 5/145* (2006.01)

(52) U.S. Cl.
CPC ........ *A61B 5/0537* (2013.01); *A61B 5/14517* (2013.01); *A61B 5/4266* (2013.01);
(Continued)

(58) Field of Classification Search
CPC .................. A61B 5/4266; A61B 2018/167
See application file for complete search history.

(56) References Cited

U.S. PATENT DOCUMENTS 3,716,861 A   2/1973   Root
3,805,427 A   4/1974   Epstein
(Continued)

FOREIGN PATENT DOCUMENTS

DE   102007046886 A1   4/2009
EP       0585670 A2    3/1994
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — Meredith Weare
(74) *Attorney, Agent, or Firm* — Peter E. Prommer; David F. Crosby

(57) ABSTRACT

A moisture sensor includes a pair of electrode plates separated by a moisture absorbent material that forms the dielectric of a capacitive sensor. As the absorbent dielectric material absorbs moisture, such as perspiration, the capacitance of the sensor changes reflecting a quantitative measure of perspiration absorbed. The sensor can be stabilized by capacitively coupling the dielectric material to the skin of the user to improve sensor stability and noise rejection. The sensor can include a capacitive sensing integrated circuit that measures the capacitance of the sensor in close proximity to the electrodes to limit the introduction of noise.

19 Claims, 18 Drawing Sheets

(52) U.S. Cl.
CPC ............ *A61B 5/443* (2013.01); *A61B 5/6803* (2013.01); *A61B 5/6832* (2013.01); *A61B 2503/10* (2013.01); *A61B 2562/0214* (2013.01); *A61B 2562/182* (2013.01)

(56) References Cited

U.S. PATENT DOCUMENTS

| | | |
|---|---|---|
| 4,304,235 A | 12/1981 | Kaufman |
| 4,416,288 A | 11/1983 | Freeman |
| 4,658,153 A | 4/1987 | Brosh |
| 5,272,375 A | 12/1993 | Belopolsky |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,042,543 A * | 3/2000 | Warwick .............. A61B 5/4266 422/424 |
| 6,063,046 A | 5/2000 | Allum |
| 6,265,090 B1 | 7/2001 | Nishide |
| 6,282,960 B1 | 9/2001 | Samuels et al. |
| 6,343,514 B1 | 2/2002 | Smith |
| 6,387,052 B1 | 5/2002 | Quinn |
| 6,410,971 B1 | 6/2002 | Otey |
| 6,421,016 B1 | 7/2002 | Phillips |
| 6,450,026 B1 | 9/2002 | Desarnaud |
| 6,455,931 B1 | 9/2002 | Hamilton |
| 6,567,158 B1 | 5/2003 | Falcial |
| 6,641,860 B1 | 11/2003 | Kaiserman |
| 6,775,906 B1 | 8/2004 | Silverbrook |
| 6,784,844 B1 | 8/2004 | Boakes |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rogers |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 2001/0012918 A1 | 8/2001 | Swanson |
| 2001/0021867 A1 | 9/2001 | Kordis |
| 2002/0000081 A1 | 1/2002 | Hirono et al. |
| 2002/0026127 A1 | 2/2002 | Balbierz |
| 2002/0082515 A1 | 6/2002 | Campbell |
| 2002/0094701 A1 | 7/2002 | Biegelsen |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0029680 A1 | 2/2005 | Jung |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0128346 A1 | 6/2006 | Yasui |
| 2006/0154398 A1 | 7/2006 | Qing |
| 2006/0160560 A1 | 7/2006 | Josenhans |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0019088 A1 | 8/2007 | Dubrow et al. |
| 2007/0270672 A1 | 11/2007 | Hayter |
| 2007/0270674 A1 | 11/2007 | Kane et al. |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0188912 A1 | 8/2008 | Stone |
| 2008/0193749 A1 | 8/2008 | Thompson |

(56) References Cited

U.S. PATENT DOCUMENTS

| | | |
|---|---|---|
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Yonggang |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0030167 A1 | 2/2010 | Thirstrup et al. |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0101789 A1 | 5/2011 | Salter |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0015007 A1 | 6/2012 | Revol-Cavalier et al. |
| 2012/0157804 A1 | 6/2012 | Rogers |
| 2012/0172697 A1 | 7/2012 | Urman |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0099358 A1 | 4/2013 | Elolampi |
| 2013/0100618 A1 | 4/2013 | Rogers |
| 2013/0012358 A1 | 5/2013 | Sarrafzadeh et al. |
| 2013/0118255 A1 | 5/2013 | Callsen |
| 2013/0150693 A1 | 6/2013 | D'angelo |
| 2013/0185003 A1 | 7/2013 | Carbeck |
| 2013/0019731 A1 | 8/2013 | Monty et al. |
| 2013/0192356 A1 | 8/2013 | De Graff |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0320503 A1 | 12/2013 | Nuzzo |
| 2013/0321373 A1 | 12/2013 | Yoshizumi |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rogers |
| 2014/0188426 A1 | 7/2014 | Fastert |
| 2014/0191236 A1 | 7/2014 | Nuzzo |
| 2014/0216524 A1 | 8/2014 | Rogers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora |
| 2015/0099954 A1* | 4/2015 | Achmann ............ A61B 5/1468 600/345 |
| 2015/0099976 A1 | 4/2015 | Ghaffari |
| 2015/0100135 A1 | 4/2015 | Ives |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Elolampi |
| 2015/0342036 A1 | 11/2015 | Fastert |
| 2016/0027834 A1 | 1/2016 | de Graff |
| 2016/0045162 A1 | 2/2016 | De Graff |
| 2016/0081192 A1 | 3/2016 | Hsu |

FOREIGN PATENT DOCUMENTS

| | | |
|---|---|---|
| EP | 0779059 A1 | 6/1997 |
| EP | 1808124 A2 | 7/2007 |
| EP | 2259062 A2 | 12/2010 |
| JP | 05-087511 A | 4/1993 |
| JP | 2009-170173 A | 7/2009 |
| WO | WO 1999/038211 A2 | 7/1999 |
| WO | WO 2005/122285 A2 | 12/2005 |
| WO | WO 2003/021679 A2 | 3/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |

(56) References Cited

FOREIGN PATENT DOCUMENTS

| | | |
|---|---|---|
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

* cited by examiner

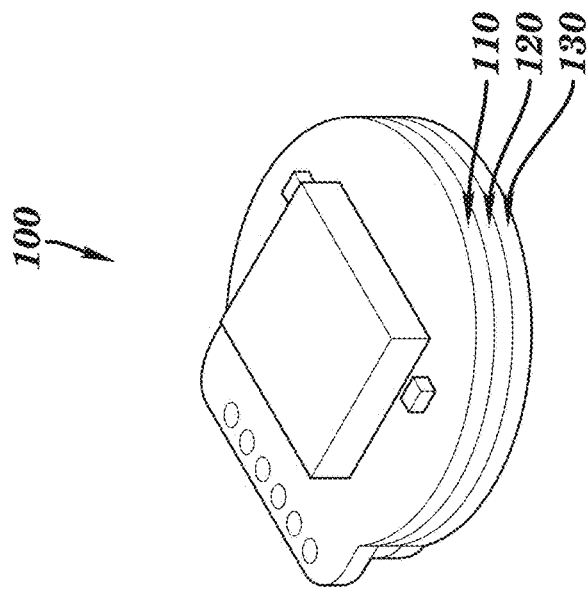
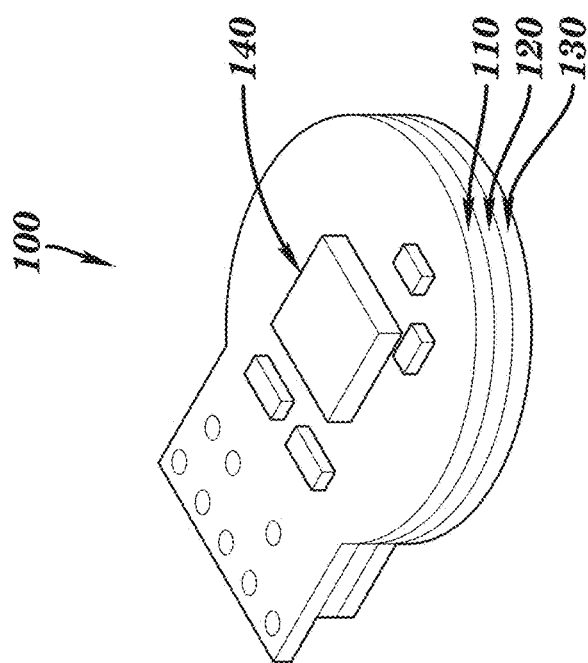

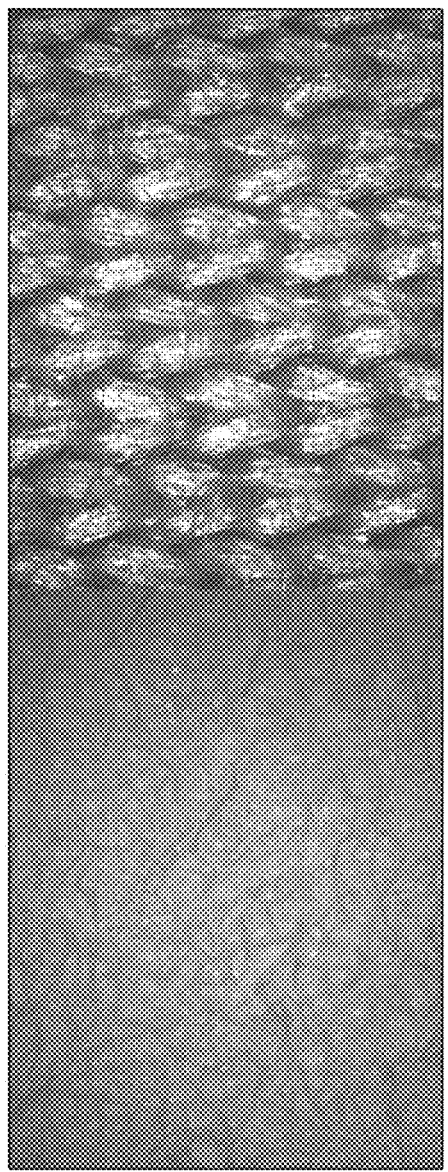
FIG. 8B CELLULOSE PAD (LEFT) AND MICROFIBER CLOTH (RIGHT)

PERSPIRATION SENSOR

CROSS-REFERENCE TO RELATED APPLICATIONS

This application claims any and all benefits as provided by law including benefit under 35 U.S.C. § 119(e) of the U.S. Provisional Application No. 62/127,124, filed Mar. 2, 1015, the contents of which are incorporated herein by reference in its entirety.

STATEMENT REGARDING FEDERALLY SPONSORED RESEARCH

Not Applicable

REFERENCE TO MICROFICHE APPENDIX

Not Applicable

BACKGROUND

Technical Field of the Invention

The present invention is directed to a moisture sensor and more specifically, to a perspiration sensor for quantitatively measuring levels of perspiration. In accordance with some embodiments, the perspiration sensor includes a capacitive sensor that can be coupled to the skin and utilize capacitance to measure perspiration. The perspiration sensor can be shielded and stabilized to reduce noise by electrically coupling the capacitor dielectric material to the skin.

Description of the Prior Art

The prior art perspiration sensors are generally related to devices for determining galvanic skin response. These devices involve the measurement of the electrical resistance of the skin, but do not provide a quantitative indication of the volume or level of perspiration over time.

SUMMARY

The present invention is directed to a method and system for obtaining a quantitative measurement of moisture, and more specifically, perspiration. Various embodiments of the invention utilize the dielectric properties of perspiration in a capacitive sensor that includes a pair of ground shielded parallel electrodes sandwiching a moisture absorbent dielectric material (e.g., a microfiber cloth). In accordance with some embodiments, the dielectric material can be electrically coupled (e.g., capacitively coupled) to the skin of the user to provide a more stable signal because the skin is capacitively coupled to earth ground which is weakly capacitively coupled to the ground of signal measurement circuit (e.g., the capacitance to digital signal converter integrated circuit). The method includes a providing a capacitor that includes a dielectric material that absorbs moisture (e.g., perspiration) in contact with the skin, wherein the capacitor includes one or more inlets that enable perspiration released from the skin to become absorbed by the absorbent dielectric material and electrically (e.g., capacitively) coupling the dielectric material to the body.

In accordance with the invention, the perspiration sensor can be constructed having three layers, a first or top layer, a second or middle layer and a third or bottom layer. The bottom layer can include an adhesive or other skin contacting material that maintains contact with and capacitively couples the sensor to the skin. The bottom layer and the top layer include the first and second electrode plates that form the capacitor with dielectric material surrounded by the middle layer sandwiched in between. The bottom layer, middle layer and top layer form a central chamber that encloses the dielectric material and positions it in a dielectric space between the first and second electrodes. The bottom layer can also include one or more pores, inlets or vents that enable perspiration released from the skin to enter central chamber and be absorbed by the dielectric material in the dielectric space. The bottom layer can also include a skin coupling electrode that becomes electrically coupled to the skin when the bottom surface of the bottom layer is adhered to or placed in contact with the skin. The skin coupling electrode can be electrically connected to the central chamber and the dielectric material. When the bottom surface includes an adhesive material, the skin coupling electrode capacitively couples the dielectric material in the central chamber to the skin to provide ground shielding adjacent to the electrodes to minimize environmental noise. In accordance with some embodiments of the invention, the dielectric material can be weakly but consistently (capacitively) coupled to earth ground through the skin.

Each of the layers can be formed from a rigid printed circuit board (PCB) or a flexible PCB, and each of the layers can be laminated together as is well known in the art. The dielectric material can be an absorbent material that rapidly replaces air with perspiration, such as a tufted microfiber cloth. The thickness of the middle layer can be selected to define and control the distance between the sensing electrode plates of the capacitor. In accordance with some embodiments, the middle layer includes a rigid material having a predefined thickness to tightly control the electrode plate spacing and slightly thinner than the thickness of the microfiber cloth causing portions of the cloth to extrude through the pores or inlets of the bottom layer facilitate moisture absorption.

In accordance with some embodiments of the invention, the device can further include a capacitance measurement integrated circuit (e.g., IC chip) mounted to the top layer that enables close proximity measurement of the change in capacitance of the sensor to minimize the introduction of noise. In this configuration, the measured capacitance can be transmitted (e.g., by wire or wirelessly) to a remote system for storing and/or analyzing the capacitance data and determining perspiration rates (e.g., volume and volume over time).

In accordance with some embodiments of the invention, the device can be fully or partially enclosed or encapsulated in polymer or elastomeric material (e.g. PDMS, or silicone) that protects the sensor from the environment. One or more of the layers can include one or more partially or fully enclosed anchor rings projecting from the perimeter of the device such that the polymer material passes through the opening in the anchor rings to more securely anchor the encapsulating material to the outside of the device.

In operation, the bottom of the device is coupled to the skin by an adhesive material and perspiration released by the skin passes through the inlets and become absorbed by the microfiber dielectric material. The capacitance of the first and second electrodes changes as the dielectric material absorbs perspiration. In addition, the bottom of the device includes a skin electrode that is electrically connected to the dielectric material and the central chamber. The skin electrode can be electrically connected to the middle layer by plated through holes or vias in the bottom layer. The vias in the middle layer can include electrodes that directly contact the dielectric material, enabling the dielectric material to be coupled (e.g., capacitively coupled) to the skin through the adhesive. The integrated circuit on the top layer includes a circuit that determines a measure of the capacitance between the first and second electrodes while the skin electrode serves to stabilize the capacitance measurement against noise.

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

FIGS. 3A and 3B show diagrammatic views of a perspiration sensor according to some embodiments of the invention.

FIGS. 8A and 8B show diagrams of dielectric material according to some embodiments of the invention.

DETAILED DESCRIPTION OF PREFERRED EMBODIMENTS

Figure 1:
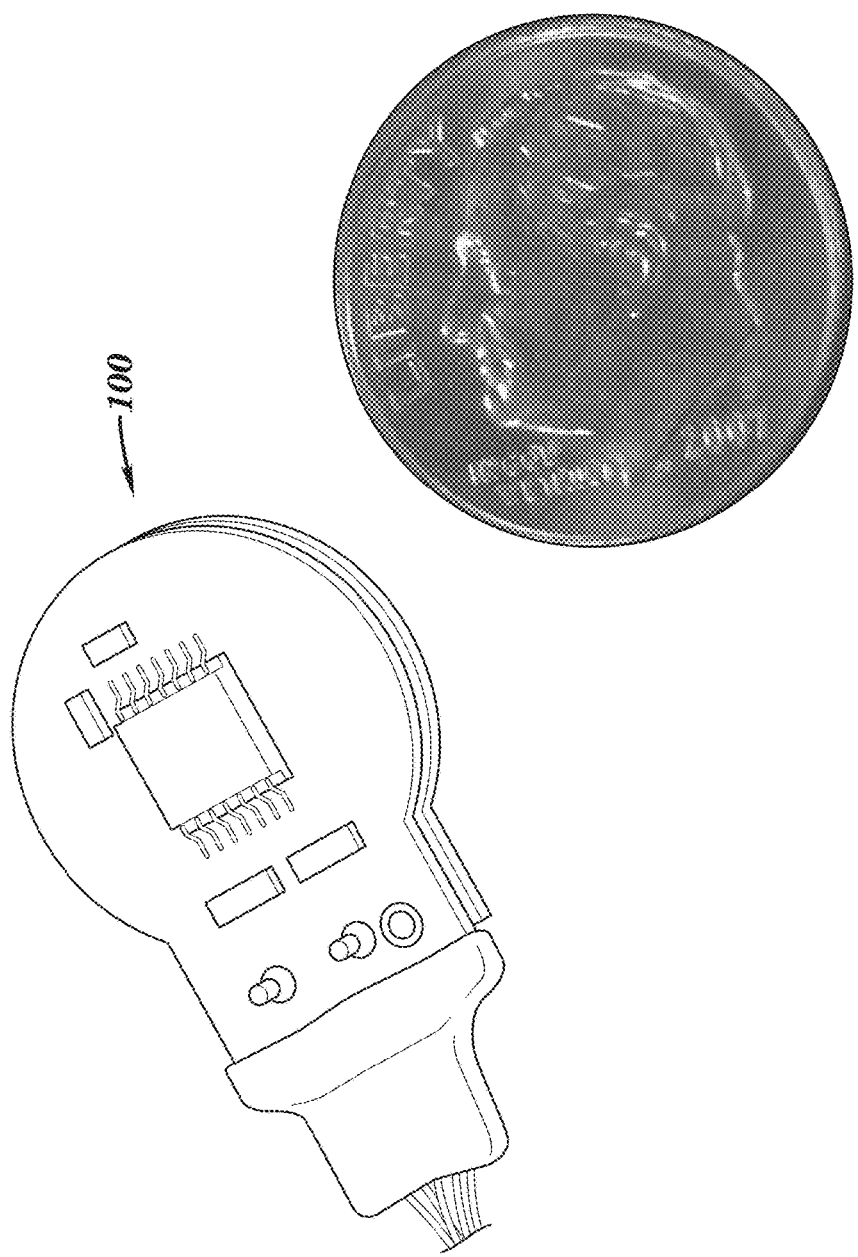
FIG. 1 is a photograph of a perspiration sensor according to an embodiment of the invention.

The present invention is directed to methods and systems for obtaining a quantitative measurement of moisture. One specific application for the invention includes the detection and measurement of perspiration. For purposes of illustration, the invention is described herein in the context of measuring perspiration, however, embodiments of the invention can be used to measure other sources of moisture.

In accordance with some embodiments of the invention, the perspiration sensor includes a pair of ground shielded parallel electrodes sandwiching a moisture absorbent dielectric material (e.g., a microfiber cloth) that forms a capacitor. The sensor allows perspiration to become absorbed by moisture absorbent dielectric material which changes the dielectric constant the dielectric material and is reflected in the measured capacitance of the electrode plates of the perspiration sensor. In accordance with some embodiments of the invention, the dielectric material can be electrically coupled (e.g., capacitively coupled) to the skin of the user to provide for more stable signal measurement. In accordance with some embodiments of the invention, the absorbent dielectric material can be weakly (e.g., 10 pF or less) but consistently (e.g., up to 10% variation) coupled through the skin to earth ground which is weakly coupled to signal ground of capacitance measuring circuit. The method includes providing a capacitor that includes an exposed dielectric material that can absorb moisture (e.g., perspiration) produced by the skin. As perspiration is released from the skin and becomes absorbed by the absorbent dielectric material, the dielectric properties of the material between the electrode plates change resulting in a change in the capacitance of the perspiration sensor. An internal or external measurement component can be connected to the electrodes of the capacitor to measure the changes in capacitance of the perspiration sensor.

The dielectric properties of perspiration closely resemble that of saline which in turn closely resemble that of water. The dielectric constant of water is about 80 times that of air. An air capacitor formed by two parallel plates will increase capacitance significantly when air is replaced with water, saline, or perspiration. The approximate capacitance C of the parallel plates can be determined by $$C = \varepsilon_0 \varepsilon_r \frac{A}{d}$$

where A is the area of the electrode plate, d is the distance between the plates; $\varepsilon_0$ is the dielectric constant of free space and $\varepsilon_r$ is the relative dielectric constant of the material between the plates.

In accordance with the invention, the dielectric material can be selected to rapidly absorb the perspiration. In accordance with some embodiments of the invention, the dielectric material can have predefined wicking or absorbency properties that provide a desired level of perspiration absorption. In operation, the dielectric material is initially in a dry state and has dielectric properties similar to air and produces an initial capacitance level. As the dielectric material is exposed to moisture (e.g., perspiration) the moisture rapidly replaces the air, changing the dielectric properties of the dielectric material and the measured capacitance level of the sensor.

In accordance with some embodiments of the invention, the absorbent dielectric material can include a tufted microfiber cloth. This material has been found to have improved capillary suction and to diffuse perspiration faster and more uniformly than other materials as well as provides higher absorption densities. Other absorbent materials, such as cellulose paper, foamy elastomers, cotton, wool, air, and moisture wicking materials, can be used. The absorbent dielectric material can be configured to have a large surface area to volume ratio of the material that results in capillary suction causing the air filled space to become filled with environmental moisture or perspiration. A capacitance measuring circuit can be provided onboard or in close proximity to the capacitor sensor to minimize noise and convert the capacitance to a digital signal for transmission to a connected device.

Figure 2B:
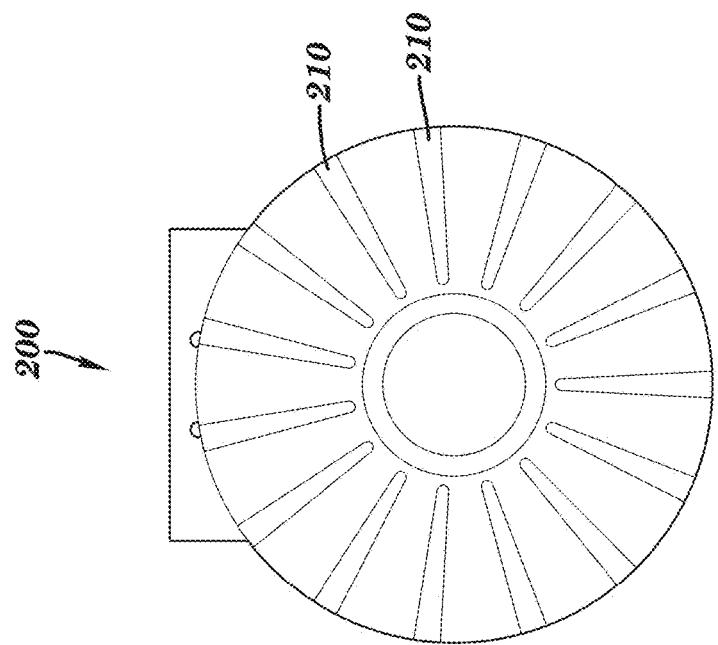
FIGS. 2A and 2B show diagrammatic views of a silicon encapsulated perspiration sensor according to an embodiment of the invention.
Figure 2A:
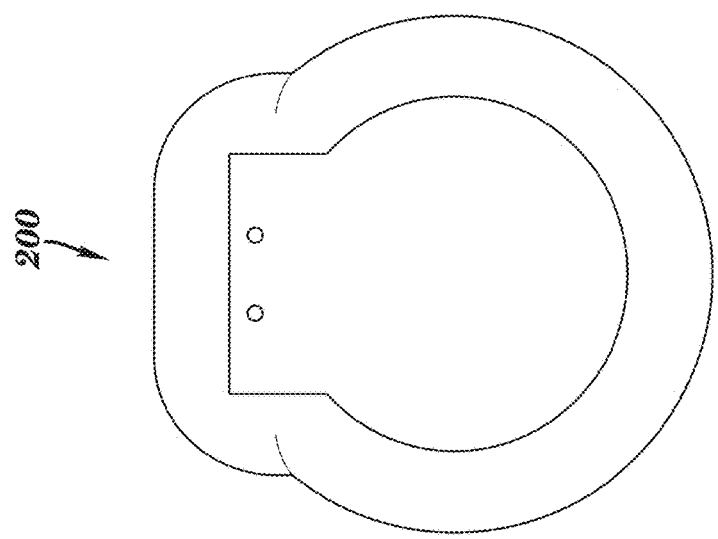

FIGS. 1, 3A and 3B shows a moisture or perspiration sensor 100 according to various embodiments of the invention with the encapsulating polymer removed to provide a better view of the structure of the device. FIGS. 2A and 2B show diagrammatic views of a perspiration sensor 200 according to embodiments of the invention encapsulated in an encapsulating material, such as polymer material (e.g., silicone, PDMS, polyimide, TPE, PET, PVC, and MMA). The perspiration sensor 200 can include channels 210 that serve to guide moisture, such as perspiration, toward inlets in the perspiration sensor 200.

As shown in FIGS. 3A and 3B, the perspiration sensor 100 can be constructed from two or more layers of insulating or dielectric material (e.g., a first layer 110, a second layer 120 and the third layer 130). In accordance with some embodiments of the invention, each layer can include a non-conductive substrate (e.g. FR4 epoxy fiberglass, PDMS, or polyimide) having a conductive layer (e.g., copper and/or tin) on one or both surfaces of the substrate, such as a printed circuit board (PCB) or flexible PCB. In accordance with some embodiments of the invention, each layer can include a protective and/or insulating coating (e.g., solder mask coating) covering a portion or all of each surface of each layer. Each of the layers that make up the perspiration sensor 100 can be bonded together using well known adhesives (e.g., epoxy, polyimide, and/or silicone based adhesives). The surfaces of at least some of the layers can include exposed pads enabling electronic components such as integrated circuits, discrete components (e.g., resistors, capacitors, diodes and other passive devices) to soldered in place. The layers can also include vias or plated through holes that allow circuit traces to extend through the layer can make contact with circuit traces of the other layers. In accordance with some embodiments of the invention, some or all of the layers can include castellated vias on or extending from the external edges that provide for mechanical alignment and enable low temperature fabrication—the castellated vias are positioned away from central chamber and can be soldered without fear of melting or otherwise damaging the absorbent dielectric material.

Figure 4:
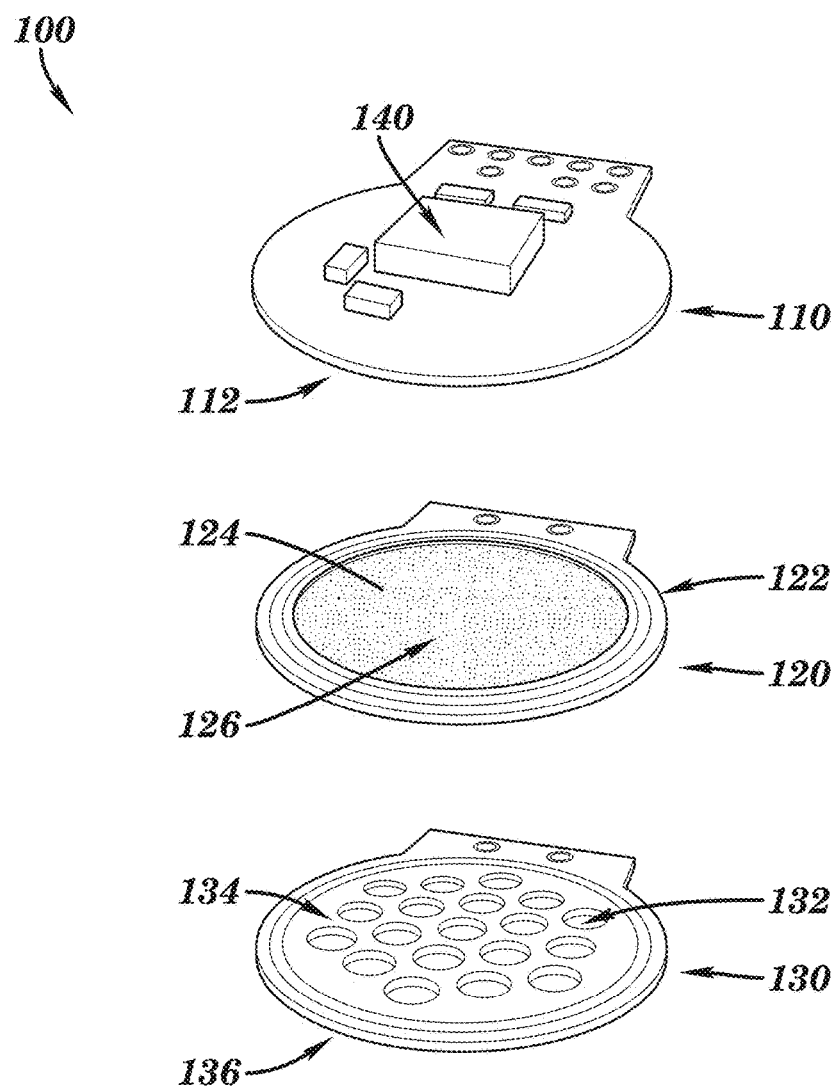
FIG. 4 shows an exploded isometric top view of a perspiration sensor according to an embodiment of the invention.

FIG. 4 shows an exploded view of a perspiration sensor 100 according to some embodiments of the invention. In this embodiment, the perspiration sensor 100 includes a first or top layer 110, a second or middle layer 120 and the third or bottom layer 130. The first layer 110 includes a first electrode 112 on the underside of the first layer (hidden from view in FIG. 4, but shown in FIG. 5). The first layer 110 can also include circuit traces that enable a sensing integrated circuit 140 to soldered in place and electrically connected to the first electrode 112 and second electrode 134 and wires (not shown) that connect the perspiration sensor 100 to other devices. The third layer 130 includes one or more inlets 132 and the second electrode 134. The third layer 130 can also include a skin electrode 136 (hidden from view in FIG. 4, but shown in FIG. 5) and an adhesive material covering the skin electrode 136 to adhere the perspiration sensor 100 to a surface such as a skin surface. The second layer 120 forms a ring 122 that at least partially surrounds or encloses the dielectric material 124 in the dielectric space defined by the central chamber 26. When the three layers are bonded together, they form a central chamber 126 which encloses the dielectric material 124 (e.g., the moisture absorbent material). In accordance with some embodiments of the invention, the thickness of each layer can be selected to minimize the overall thickness of the sensor to improve user comfort. Thus, the first layer 110 and the third layer 130 can be thicker or thinner than the middle layer 120. Alternatively, each of the layers can have the same or different thicknesses. In accordance with some embodiments, the sensor detection area, defined by the inlets 132 can cover an area of 1 cubic centimeter and provide an average pore density of 50 pores (e.g., in the arm pit).

Figure 5:
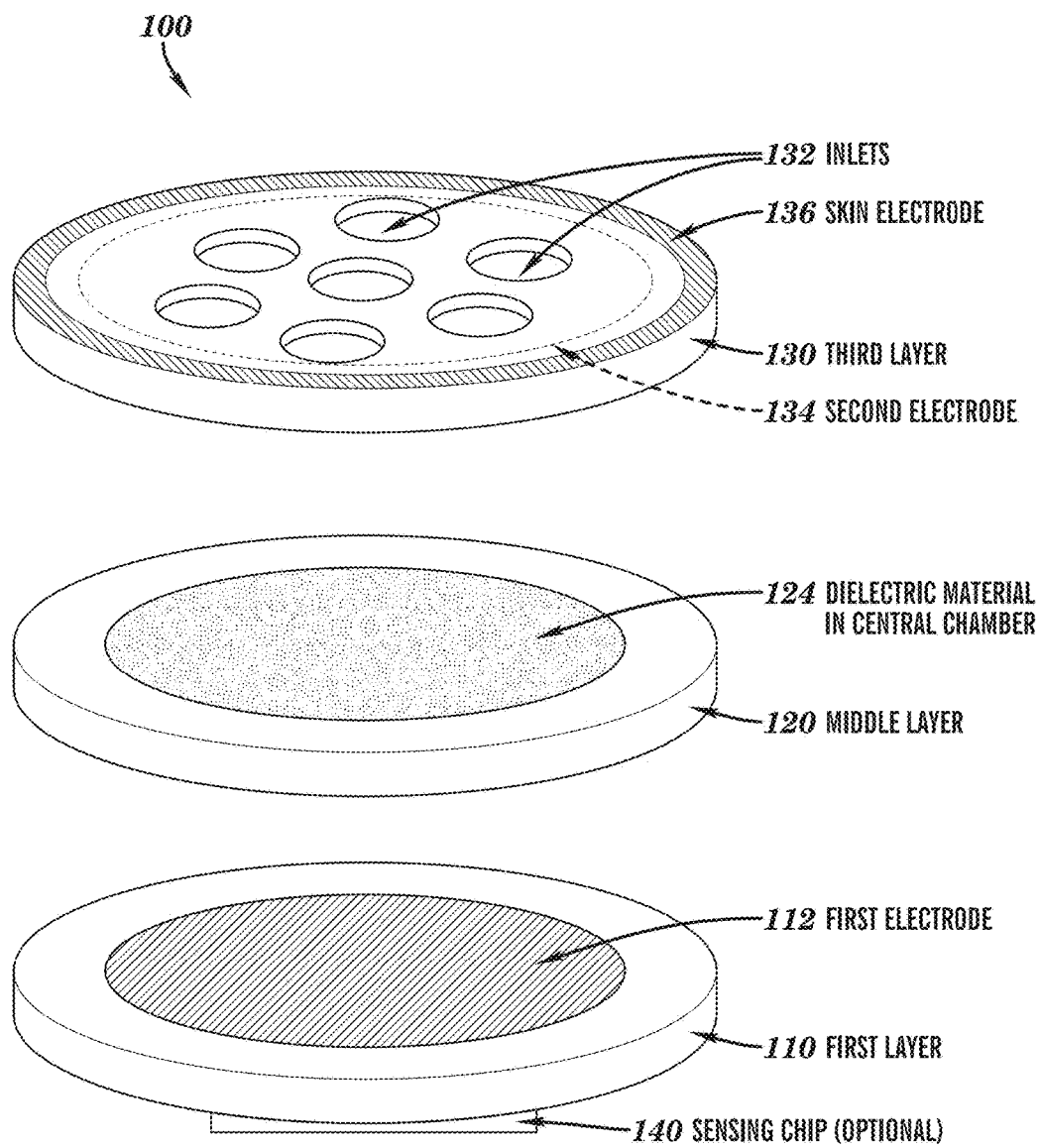
FIG. 5 shows an exploded isometric bottom view of a perspiration sensor according to an embodiment of the invention.

FIG. 5 shows an exploded bottom view of the perspiration sensor 100 (e.g., showing the third layer 130 on top). As shown in FIG. 5, the third layer 130 can include a skin electrode 136 on the outer surface thereof. The skin electrode 136 can be provided in the form of a ring, as shown, or as a set of interconnected contact points over the outer surface of the third layer 130. In accordance with some embodiments, the skin electrode 136 can be electrically connected to the dielectric material 124 in the central chamber 126 of the perspiration sensor 100 by extending circuit traces around or vias through the third layer 130 to the middle layer 120 and in contact with the dielectric material 124. In accordance with other embodiments, the skin electrode 136 can be electrically connected to the dielectric material 124 by circuit traces or wires that extend from the inner surface of the third layer 130 into the central chamber 126. The skin electrode 136 can be covered with a solder mask or other insulating material (e.g., skin adhesive tape). When the perspiration sensor 100 is adhered or placed in contact with the skin, the skin electrode 136 capacitively couples the dielectric material 124 to the skin.

Figure 6A:
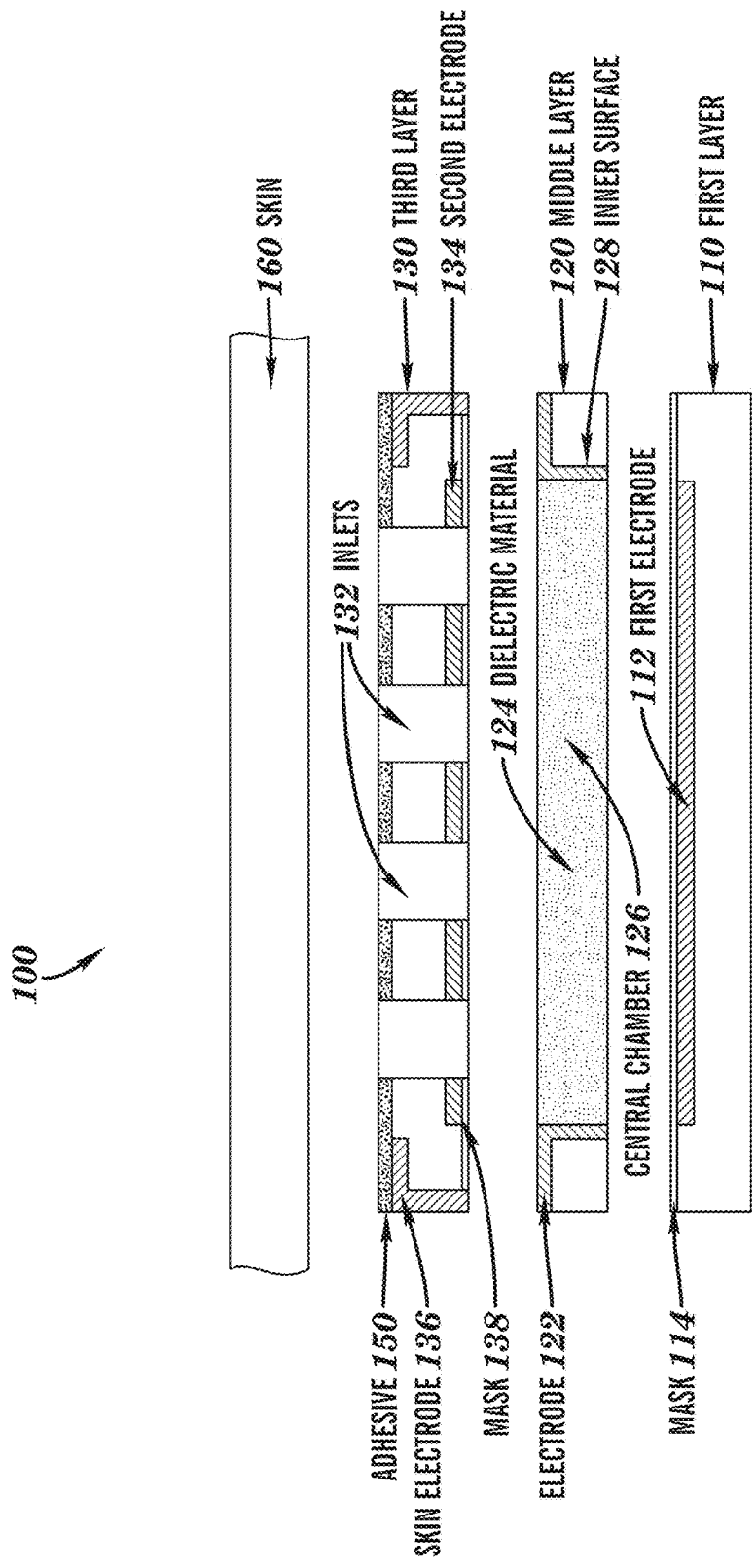
FIG. 6A shows an exploded cross-section view of a perspiration sensor according to an embodiment of the invention.
Figure 6B:
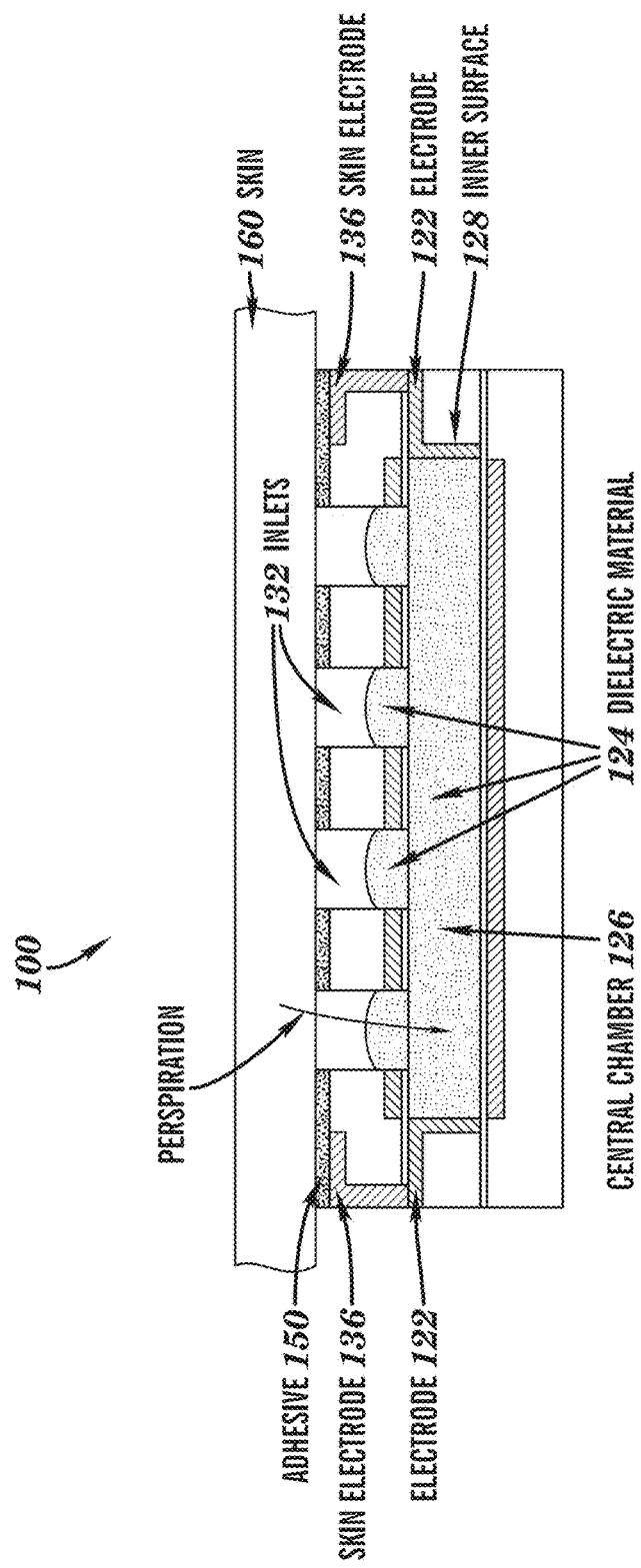
FIG. 6B shows a cross-section view of an assembled perspiration sensor according to an embodiment of the invention shown in FIG. 6A.

FIG. 6A shows an exploded cross-section view and FIG. 6B shows an assembled cross-section view of a perspiration sensor 100 according to some embodiments of the invention. In this embodiment, an adhesive layer 150 adheres the third layer 130 of the perspiration sensor 100 to the surface of the skin 160 enabling the device to measure perspiration. The perspiration sensor 100 includes a first layer 110, second layer 120 and a third layer 130. The first electrode 112 is formed on the inner surface of the first layer 110 and the second electrode 134 is formed on the inner surface of the third layer 130. A mask 114 on the first layer and a mask 138 on third layer can be included to electrically insulate the first electrode 112 and the second electrode 134 from the dielectric material 124 while enabling the dielectric material 124 to be in intimate contact with the first electrode 112 and the second electrode 134 while preventing the moistened dielectric material from shorting the first electrode to the second electrode. The insulating masks 114 and 138 can be formed from any solder mask insulating material (e.g., a layer or film of epoxy or UV cured polymer or resin). The second layer 120 is bonded between the first layer 110 and the third layer 130 supporting the first electrode 112 at predefined distance with respect to the second electrode 134 and forming the central chamber 126 that encloses the moisture absorbent dielectric material 124. The third layer 130 includes one or more inlets 132 that allow the moisture (e.g., perspiration) to enter the central chamber 126 and become absorbed by the moisture absorbent dielectric material 124 as well as to allow air initially contained within the moisture absorbent dielectric material 124 to escape. As shown in FIG. 6B, when the layers are bonded together, the moisture absorbent dielectric material 124 can become partially or fully extruded through the inlets 132 to facilitate moisture absorption. In accordance with some embodiments, an outlet can be provided through the middle layer 120 or the first layer 110 to enable air initially contained within the moisture absorbent dielectric material 124 to escape. The perspiration from skin 160 enters the inlets 132 and is absorbed by the moisture absorbent dielectric material 124.

As shown in FIGS. 6A and 6B, the third layer 130 includes one or more vias or plated through holes that electrically connect the skin electrode 136 to the inner surface of the third layer 130 and after assembly, make electrical contact with an inner trace or electrode 122 on the middle layer 120. The inner electrode 122 can extend into the central chamber 126 and make contact with the moisture absorbent dielectric material 124. In some embodiments of the invention, all or a portion of the inner surface 128 of the middle layer 120 can include a conductive material (e.g., copper or tin) that makes contact with the moisture absorbent dielectric material 124.

Figure 7A:
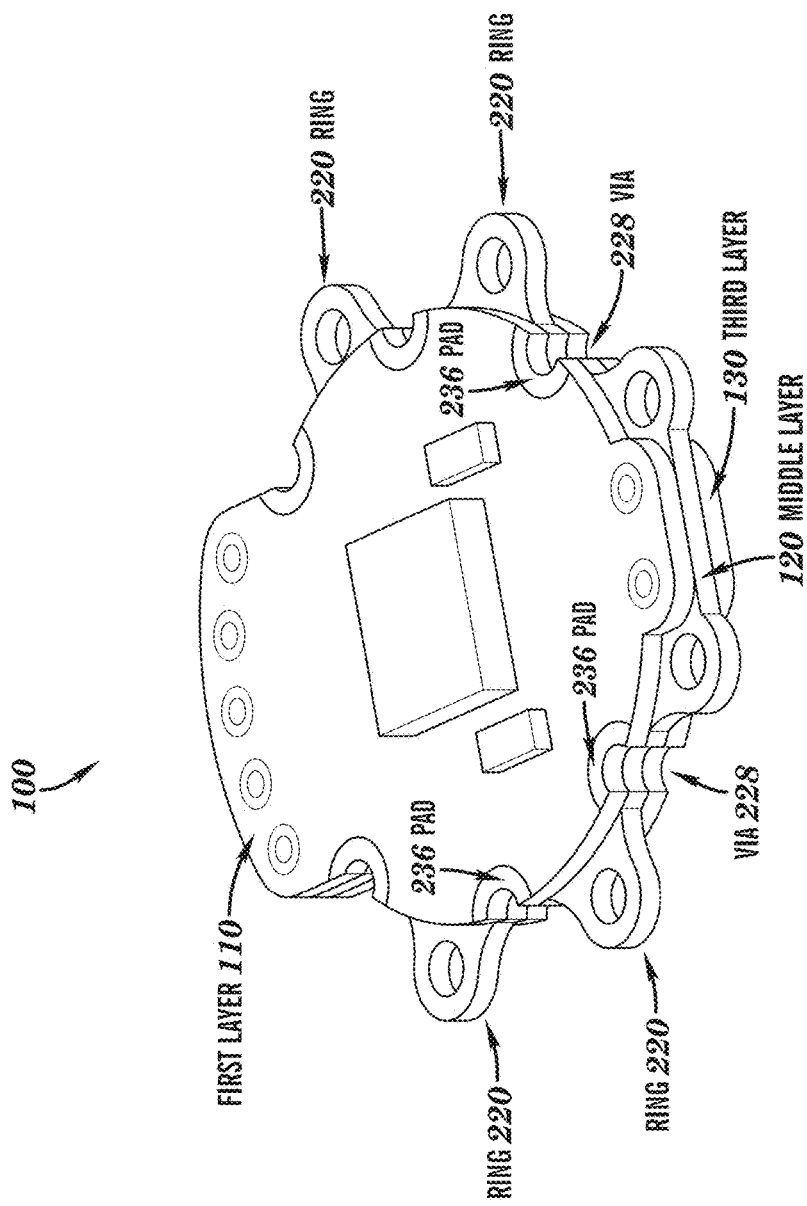
FIG. 7A shows a diagram of a perspiration sensor according to some embodiments of the invention.
Figure 7B:
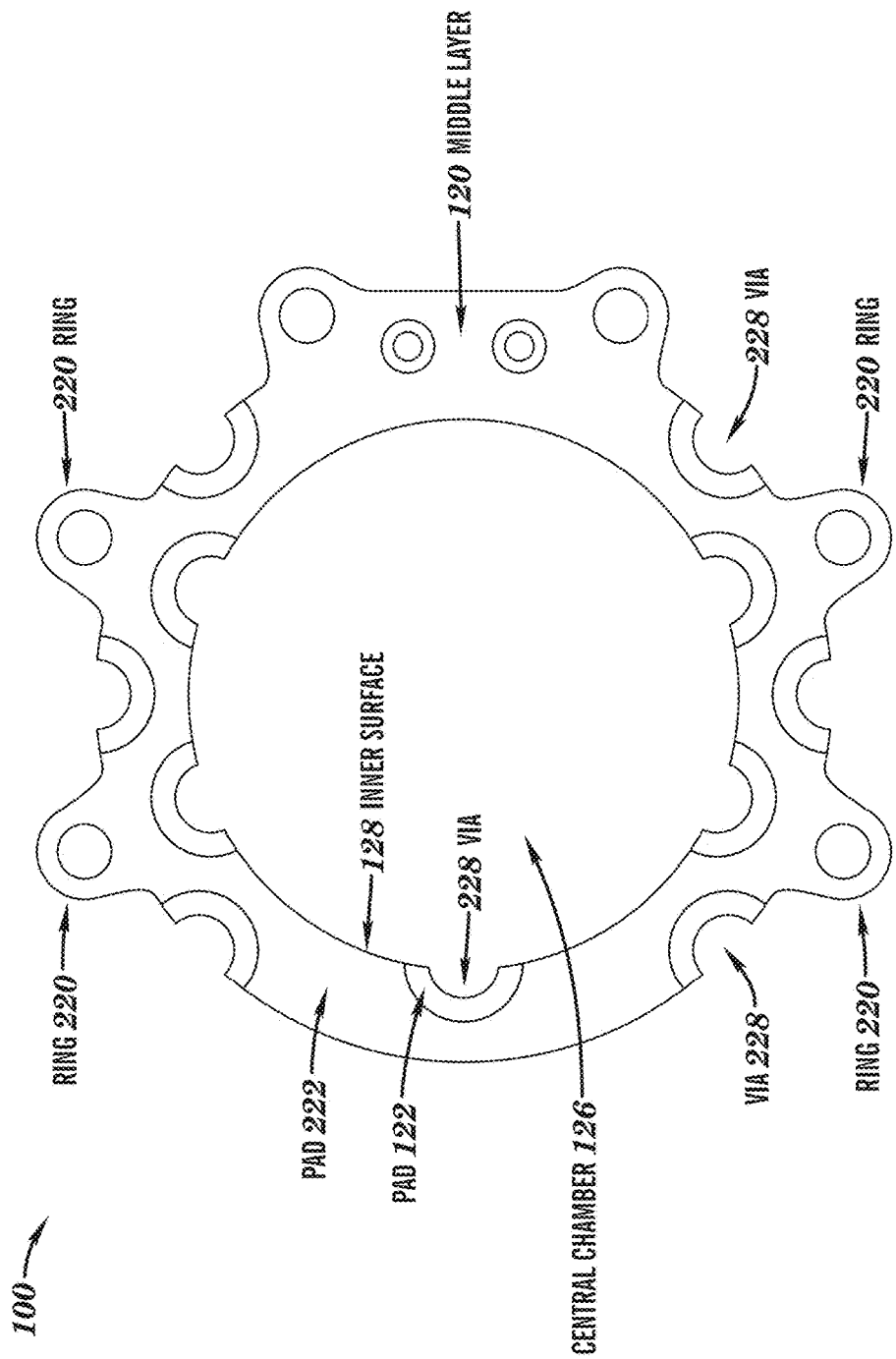
FIG. 7B shows a diagrammatic view of the middle layer according to an embodiment of the invention.

FIG. 7A shows a perspective view of a perspiration sensor 100 according to some embodiments of the invention and FIG. 7B shows a diagrammatic view of the middle layer 120. In these embodiments, the first layer 110, the middle layer 120 and the third layer 130 each include pads 122, 236 and plated through holes or partial holes or vias 228 that enable circuit traces to extend between layers. Solder can be applied to the plated through holes or vias 228 to create a physical connection between the layers and an electrical connection between the pads 122, 236 on the outside surfaces of the sensor 100 and the dielectric space defined by the central chamber 126. In some embodiments, the third layer 130 can include pads (not shown) that serve as the skin electrode 136 and can be electrically connected to circuit traces on the middle layer 120 and the first layer 110 soldering together the vias 228. Similar vias 226 can be provided on the inner surface of the middle layer 120 and connected by circuit traces 222 to one or more of the vias 228 to provide an electrical connection between the skin electrode 136 and the moisture absorbent dielectric material 124.

Figure 7C:
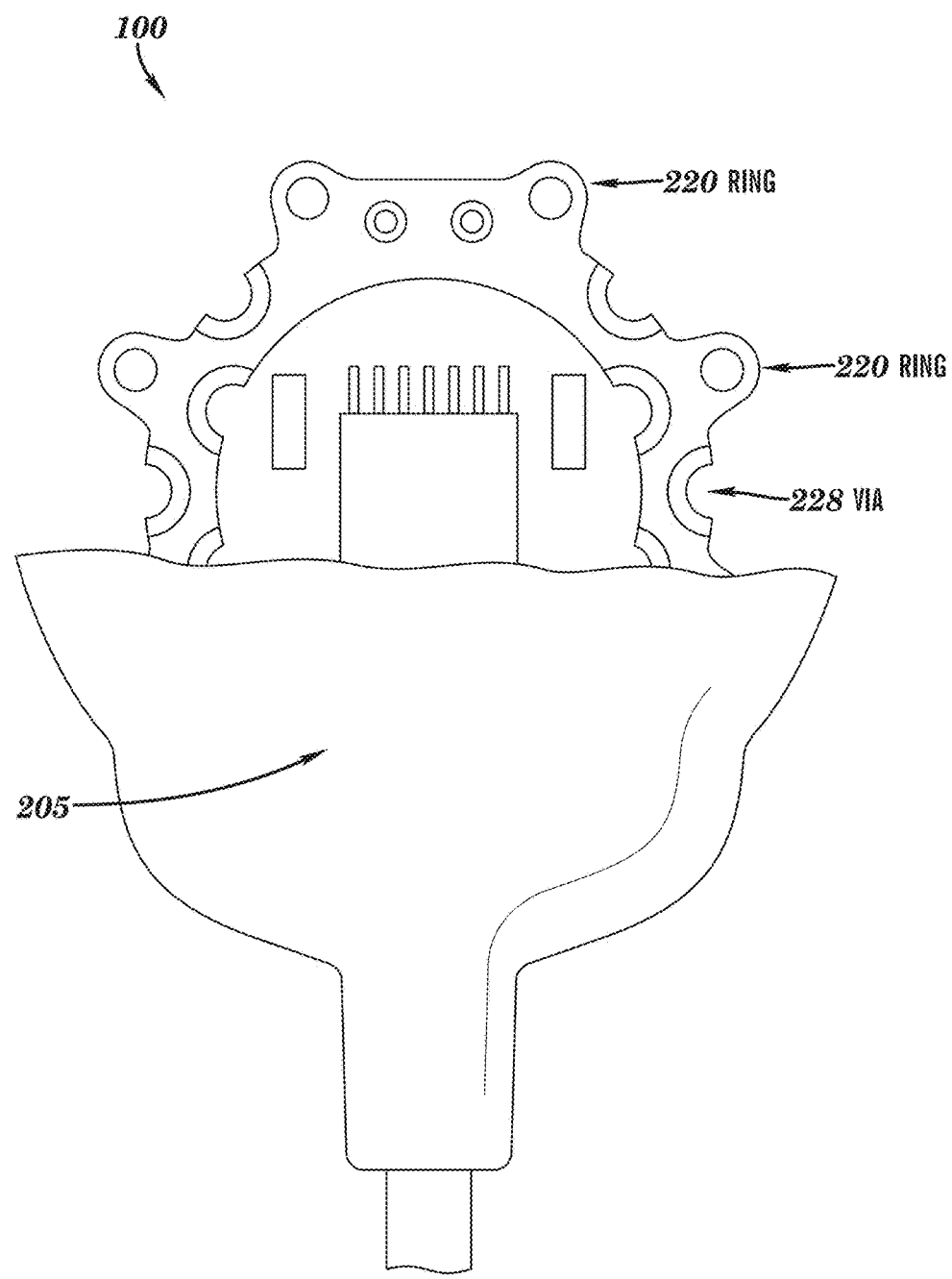
FIG. 7C shows a cutaway view of a perspiration sensor according to some embodiments of the invention with a portion of the encapsulation material removed.

In accordance with some embodiments of the invention, the perspiration sensor 100 can also include one or more anchor rings 220 that project from the peripheral edge of the device as shown in FIGS. 7A and 7B. The anchor rings 220 serve to provide features in the peripheral structure of the sensor device to aid in anchoring the device in the encapsulating material such as silicone, PDMS, polyimide during assembly. FIG. 7C shows a partially cut away view of a perspiration sensor 100 according to some embodiments of the invention. In this embodiment, the vias 228 are shown along the outer surface of the sensor 100 and the anchor rings 220 are shown extending from the outer peripheral surface of the sensor 100. In some embodiments, the encapsulating material 205 can at least partially extend into the openings of the anchor rings 220.

Figure 8A:
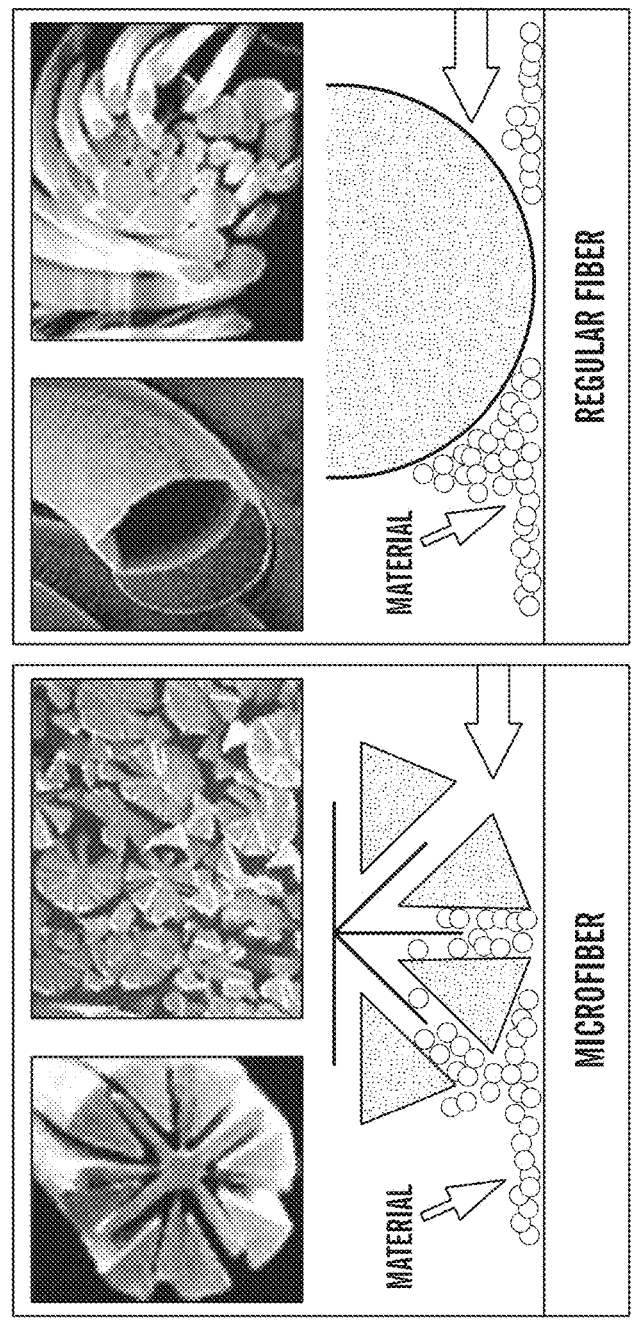

FIGS. 8A and 8B show photos and diagrams of microfibers. Microfiber based materials provide for improved absorption of moisture. In some embodiments, the microfibers can be split microfibers which have an X or asterisk shaped cross-section as shown in FIG. 8A. This structure results in the formation of microchannels in the fibers that help absorb moisture (e.g., by capillary action) better than regular solid fibers. As shown in FIG. 8B, these microfibers can be loosely woven into a tufted cloth that provides good absorption of moisture.

Figure 9A:
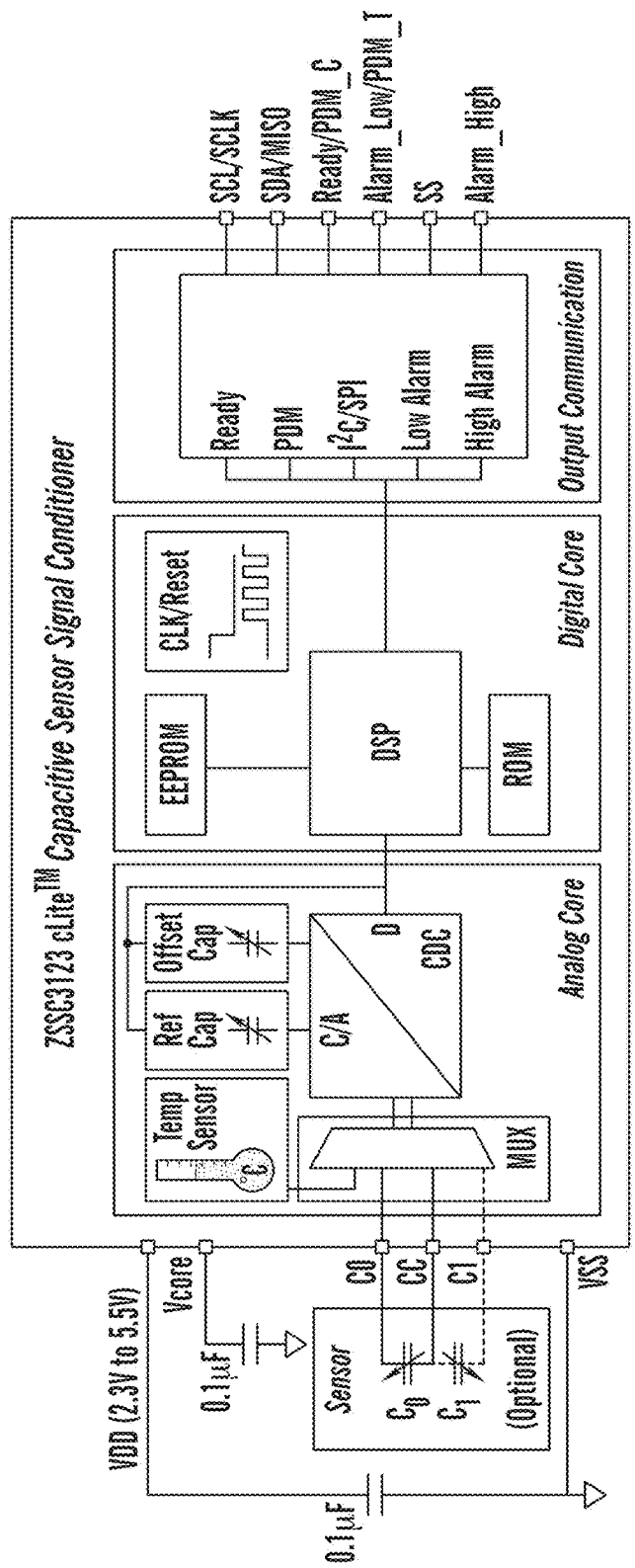
FIGS. 9A and 9B show diagrams of electronic circuits for measuring the change in capacitance between the electrodes of a perspiration sensor according to some embodiments of the invention.
Figure 9B:
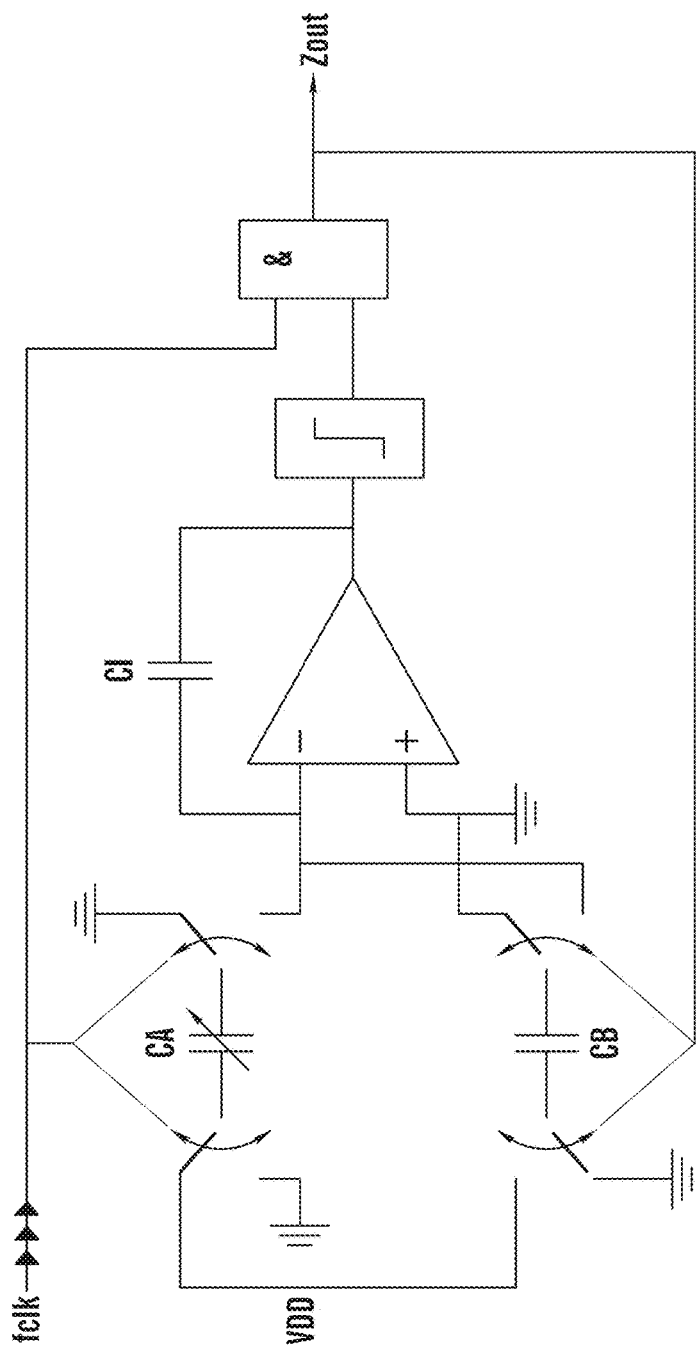

In accordance with some embodiments, the perspiration sensor can include a capacitive sensor signal measuring integrated circuit that accurately measures the capacitance or capacitive signal and converts it to a digital signal for transmission to a remote device. In accordance with some embodiments of the invention, the capacitive sensor signal measuring integrated circuit can include a ZSSC3123 integrated circuit (ZMDI, Dresden, Germany and Milpitas, Calif.). FIG. 9A shows a block diagram of the integrated circuit. FIG. 9B shows a diagram of a charge balancing circuit for converting the analog capacitance signal to a digital signal. The circuit includes a 1st order charge-balancing capacitance-to-digital converter. Capacitor CB can be a fixed reference capacitor internal to the IC itself. The measurement determines the amount of time it takes each cycle to charge and discharge the reference capacitor. The capacitor CA is driven by a square wave voltage with excitation frequency in the 100 kHz range to prevent aging effects that occur when driven by a DC signal. The output signal generated by this circuit is a ratio of sensor capacitance to reference capacitance.

Figure 10A:
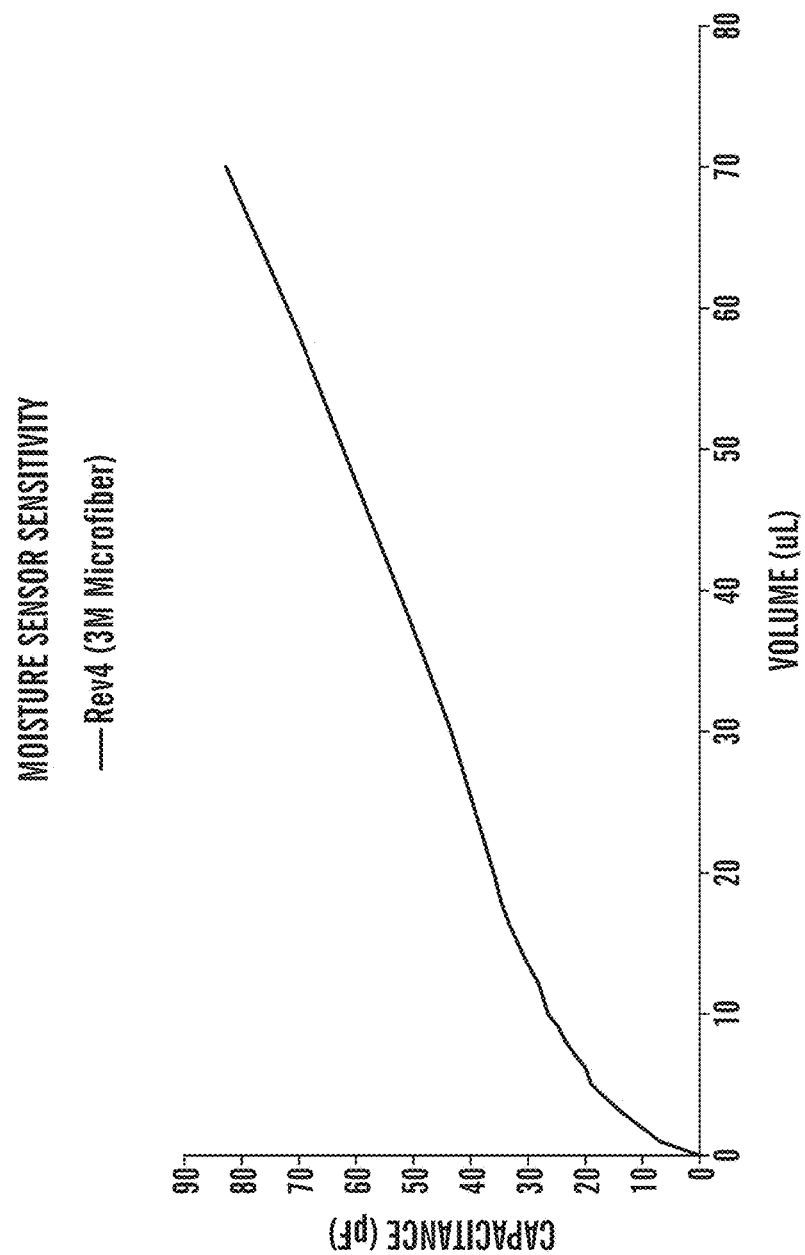
FIGS. 10A, 10B, 10C and 10D show graphs of performance data for 5 a perspiration sensor according to some embodiments of the invention.

FIG. 10A shows a sensitivity graph for a capacitive perspiration sensor according to the invention. As shown in FIG. 10A, the sensitivity is higher (e.g., 2.5 pF/µL) at lower moisture levels and decreases (e.g., to 1.2 pF/µL) as the level of moisture increases.

Figure 10B:
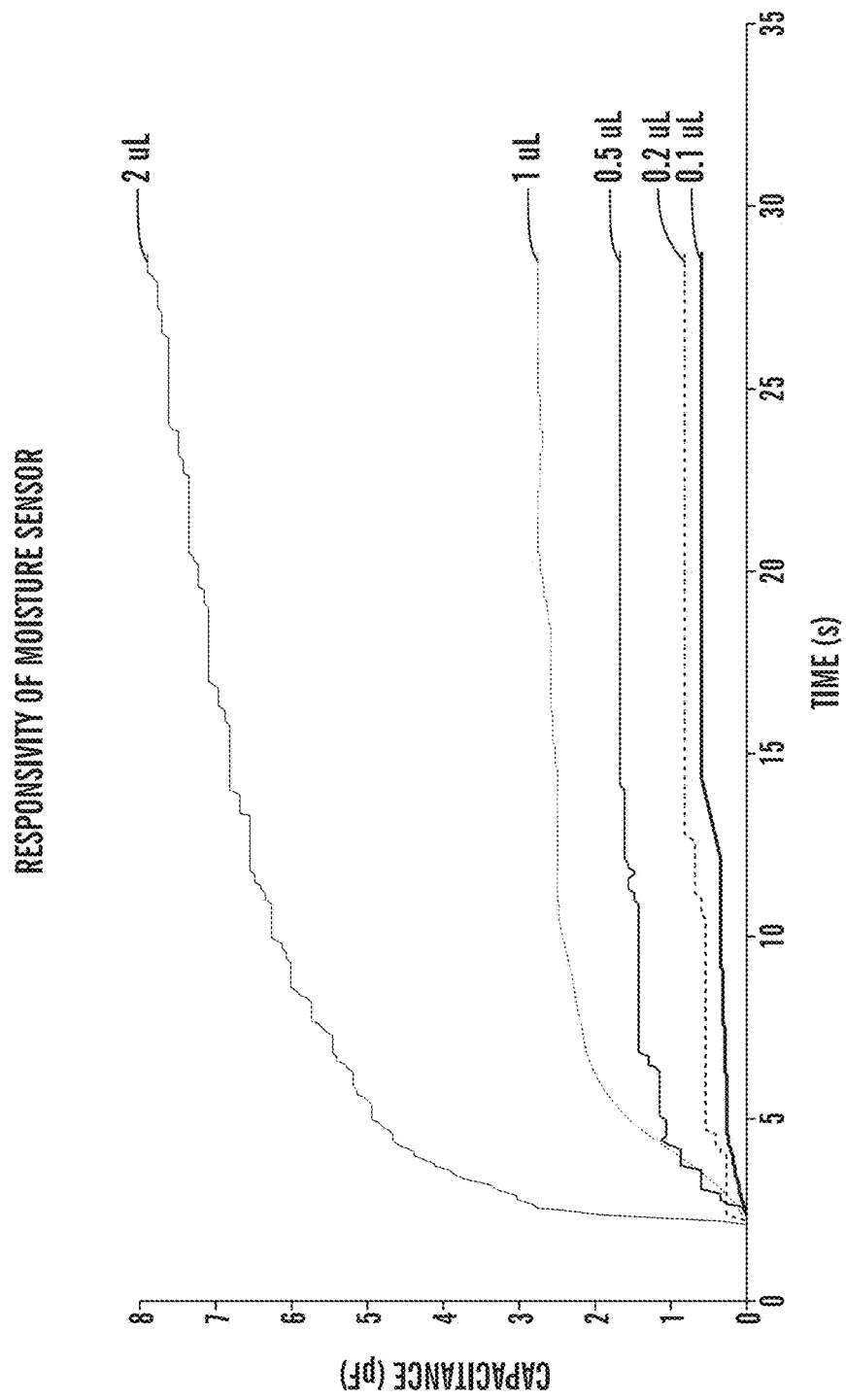

FIG. 10B shows a responsivity graph for a capacitive perspiration sensor according to the invention. The graph in FIG. 10B shows the response of the capacitive perspiration sensor according to the invention over time at 5 different moisture levels (e.g., 0.1 µL, 0.2 µL, 0.5 µL, 1.0 µL, and 2.0 µL).

Figure 10C:
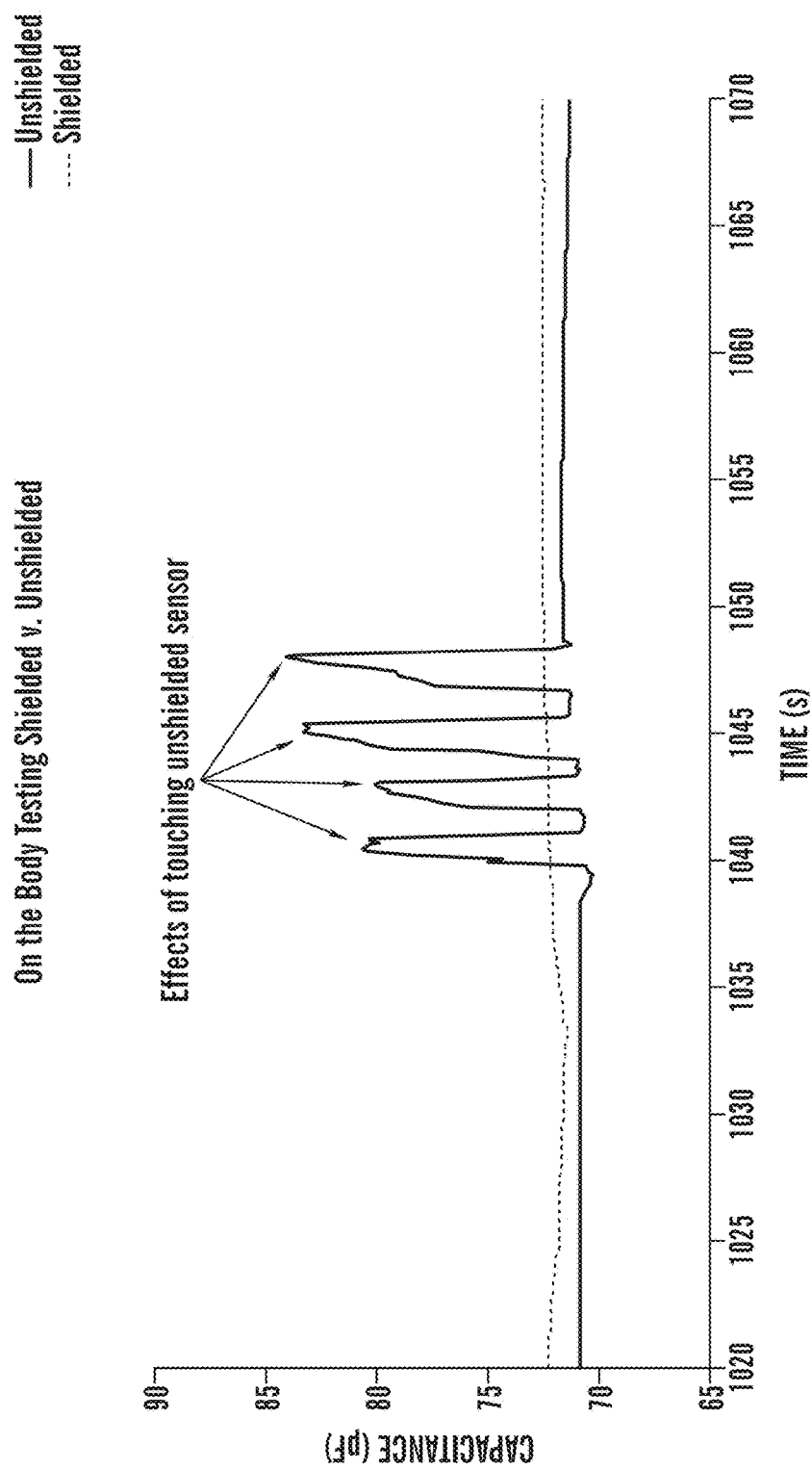

FIG. 10C shows the effect of shielding (e.g., capacitive coupling the dielectric to the skin) on a capacitive perspiration sensor according to the invention. As shown in FIG. 10C, an unshielded capacitive perspiration sensor exhibits signal spikes upon contact whereas the shielded capacitive perspiration sensor according to the invention does not.

Figure 10D:
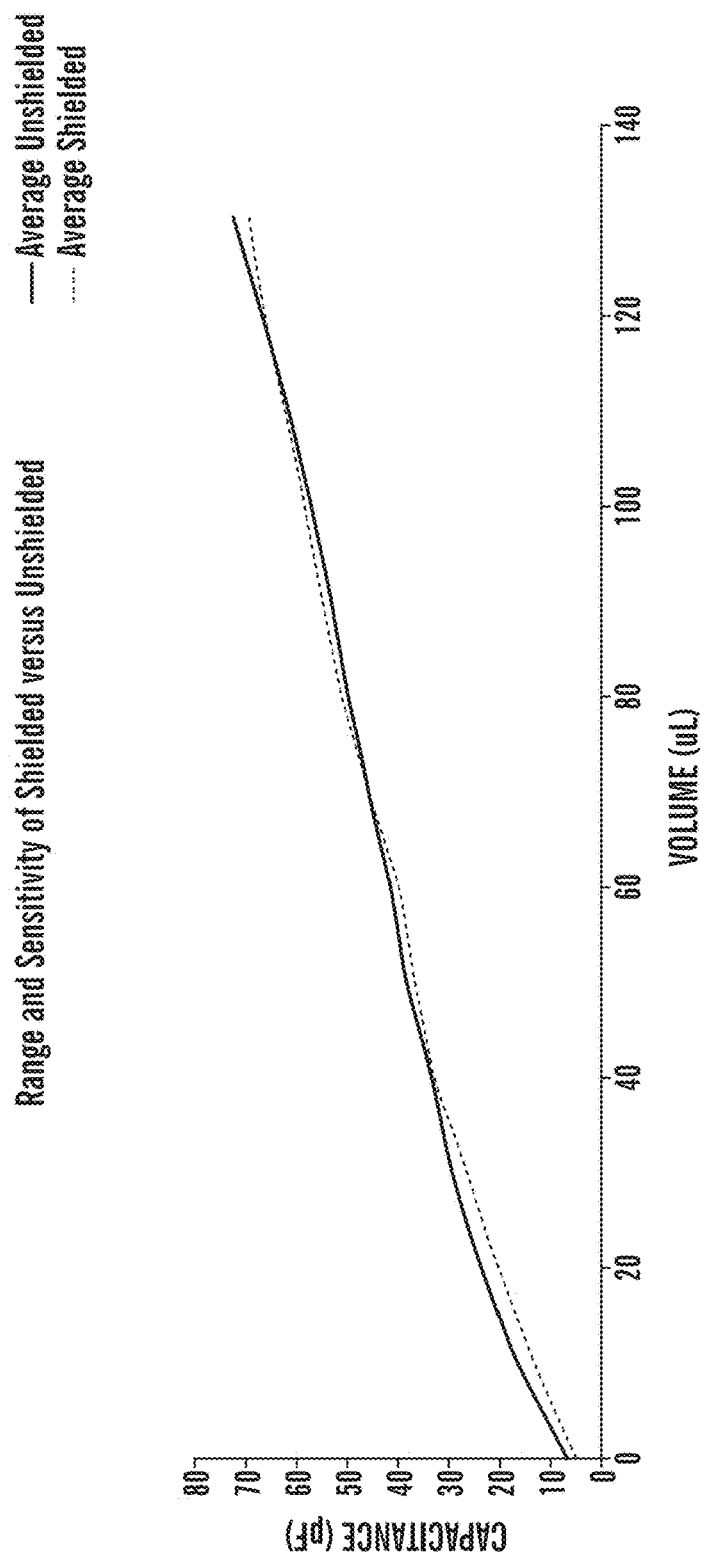

FIG. 10D shows a comparison of the range and sensitivity of shielded and unshielded capacitive perspiration sensors according to the invention. As shown in FIG. 10D, the shielded sensor has approximately the same range and sensitivity as an unshielded sensor.

In accordance with some embodiments of the invention, the perspiration sensor can be part of system that quantitatively measures perspiration of a user in real time. The sensor can be connected to a data-logging hub (e.g. Bio-Stamp TM by MC10 Inc., a smartphone or data recorder). The perspiration sensor can measure a change in capacitance over time and calculate perspiration moisture volume using a predetermined calibrated curve. The data logging hub can include a computer processor and associated memory that can communicate with the perspiration sensor to receive sensor data. The data logging hub can include additional wired or wireless communication components to enable the sensor data to be stored in a remote database or processed by a remote data processing system.

While some embodiments of the present invention are described in the context of a perspiration sensor, the invention can be used for measuring moisture in other applications. In some embodiments, the moisture sensor can be used to measure perspiration to test the efficacy of antiperspirant products. In other applications, the moisture sensor can be installed in a helmet worn by an athlete, a soldier or a fighter pilot as well as other areas of the body to provide continuous physiological monitoring, for example, for health, wellness, hydration and/or stress monitoring. In accordance with some embodiments, the central chamber or an adjacent collection chamber can include analyte sensors and/or assays to detecting the presence and/or quantity of components of the absorbed perspiration. For example, a sodium sensor can be included for diagnosis of cystic fibrosis.

Other embodiments are within the scope and spirit of the invention. For example, due to the nature of hardware and software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

The invention claimed is:

1. A perspiration sensor comprising:
   a first electrode positioned a predefined distance from a second electrode defining a dielectric space between the first electrode and the second electrode;
   a moisture absorbent dielectric material positioned in the dielectric space between the first electrode and the second electrode;
   at least one inlet enabling moisture from outside the dielectric space to enter the dielectric space and become absorbed by the moisture absorbent material;
   a skin electrode and an adhesive layer configured for adhering the skin electrode to a skin portion of a user whereby the skin electrode is capacitively coupled to the skin portion of the user, and wherein the skin electrode is electrically connected to the moisture absorbent material;
   a polymer material encapsulating at least a portion of the perspiration sensor; and
   wherein the perspiration sensor includes one or more loops extending from a peripheral edge of the perspiration sensor and the polymer material at least partially extends into an opening in at least one loop.

2. The perspiration sensor according to claim 1 wherein the moisture absorbent material includes a tufted microfiber cloth.

3. The perspiration sensor according to claim 1 wherein the moisture includes perspiration.

4. The perspiration sensor according to claim 1 wherein the polymer material forms channels in at least one surface of the perspiration sensor to direct moisture to the at least one inlet of the perspiration sensor.

5. The perspiration sensor according to claim 1 wherein the polymer material includes silicone.

6. A perspiration sensor comprising:
   a first electrode positioned a predefined distance from a second electrode defining a dielectric space between the first electrode and the second electrode wherein:
      the first electrode is mounted to a non-conducting first substrate layer;
      the second electrode is mounted to a non-conducting third substrate layer; and
      the first substrate layer is separated from the third substrate layer by a non-conducting second substrate layer;
   a moisture absorbent dielectric material positioned in the dielectric space between the first electrode and the second electrode;
   at least one inlet enabling moisture from outside the dielectric space to enter the dielectric space and become absorbed by the moisture absorbent material; and
   a skin electrode and an adhesive layer configured for adhering the skin electrode to a skin portion of a user whereby the skin electrode is capacitively coupled to the skin portion of the user, and
   wherein the second substrate layer includes a third electrode and the third electrode connects the skin electrode to the moisture absorbent material in the dielectric space.

7. The perspiration sensor according to claim 6 wherein the second substrate layer has a predefined thickness that defines a distance between the first electrode and the second electrode.

8. The perspiration sensor according to claim 6 wherein the non-conducting first substrate layer includes an epoxy fiberglass material, the non-conducting second substrate layer includes an epoxy fiberglass material, and the non-conducting third substrate layer includes an epoxy fiberglass material.

9. The perspiration sensor according to claim 6 wherein the non-conducting first substrate layer includes a polyimide material, the non-conducting second substrate layer includes a polyimide material, and the non-conducting third substrate layer includes a polyimide material.

10. The perspiration sensor according to claim 6 wherein the second substrate layer forms a ring that defines the dielectric space.

11. The perspiration sensor according to claim 6 wherein at least one of the first substrate layer and the second substrate layer include an outlet to enable air contained in the dielectric space to escape as moisture enters the dielectric space.

12. The perspiration sensor according to claim 6 further comprising an integrated circuit coupled to the first substrate layer and electrically connected to the first electrode and the second electrode; and
   wherein the integrated circuit receives a signal from the first electrode and the second electrode and outputs a digital signal as a function of the received signal.

13. A perspiration sensor comprising:
   a first electrode positioned a predefined distance from a second electrode defining a dielectric space between the first electrode and the second electrode wherein:
      the first electrode is mounted to a non-conducting first substrate layer;
      the second electrode is mounted to a non-conducting third substrate layer; and
      the first substrate layer is separated from the third substrate layer by a non-conducting second substrate layer;
   a moisture absorbent dielectric material positioned in the dielectric space between the first electrode and the second electrode;
   at least one inlet enabling moisture from outside the dielectric space to enter the dielectric space and become absorbed by the moisture absorbent material; and
   a skin electrode and an adhesive layer configured for adhering the skin electrode to a skin portion of a user whereby the skin electrode is capacitively coupled to the skin portion of the user, and wherein the skin electrode is electrically connected to the moisture absorbent material; and
   wherein the first substrate layer includes an insulating mask that enables the first electrode to be in intimate contact with the moisture absorbent material and the second substrate layer includes an insulating mask that enables the second electrode to be in intimate contact with the moisture absorbent material.

14. The perspiration sensor according to claim 13 wherein the second substrate layer has a predefined thickness that defines a distance between the first electrode and the second electrode.

15. The perspiration sensor according to claim 13 wherein the non-conducting first substrate layer includes an epoxy fiberglass material, the non-conducting second substrate layer includes an epoxy fiberglass material, and the non-conducting third substrate layer includes an epoxy fiberglass material.

16. The perspiration sensor according to claim 13 wherein the non-conducting first substrate layer includes a polyimide material, the non-conducting second substrate layer includes a polyimide material, and the non-conducting third substrate layer includes a polyimide material.

17. The perspiration sensor according to claim 13 wherein the second substrate layer forms a ring that defines the dielectric space.

18. The perspiration sensor according to claim 13 wherein at least one of the first substrate layer and the second substrate layer include an outlet to enable air contained in the dielectric space to escape as moisture enters the dielectric space.

19. The perspiration sensor according to claim 13 further comprising an integrated circuit coupled to the first substrate layer and electrically connected to the first electrode and the second electrode; and
    wherein the integrated circuit receives a signal from the first electrode and the second electrode and outputs a digital signal as a function of the received signal.

* * * * *